(12) United States Patent
Almirante et al.

(10) Patent No.: US 7,723,529 B2
(45) Date of Patent: May 25, 2010

(54) PROCESS FOR PREPARING NITROOXY ESTERS, NITROOXY THIOESTERS NITROOXY CARBONATES AND NITROOXY THIOCARBINATES, INTERMEDIATES USEFUL IN SAID PROCESS AND PREPARATION THEREOF

(75) Inventors: Nicoletta Almirante, Milan (IT); Massimiliano Ferrario, Ceriano Laghetto (IT); Ennio Ongini, Segrate (IT)

(73) Assignee: Nicox S.A., Sophia Antipolis - Valbonne (FR)

( * ) Notice: Subject to any disclaimer, the term of this patent is extended or adjusted under 35 U.S.C. 154(b) by 475 days.

(21) Appl. No.: 11/632,666

(22) PCT Filed: Feb. 2, 2005

(86) PCT No.: PCT/EP2005/050459

§ 371 (c)(1),
(2), (4) Date: Jan. 17, 2007

(87) PCT Pub. No.: WO2006/008196

PCT Pub. Date: Jan. 26, 2006

(65) Prior Publication Data

US 2007/0238882 A1    Oct. 11, 2007

(30) Foreign Application Priority Data

Jul. 20, 2004   (WO) ................ PCT/EP2004/051550

(51) Int. Cl.
C07D 257/00 (2006.01)
C07D 403/00 (2006.01)

(52) U.S. Cl. ..................................... 548/250; 548/452

(58) Field of Classification Search ................ 548/250, 548/452
See application file for complete search history.

(56) References Cited

U.S. PATENT DOCUMENTS 4,046,889 A    9/1977 Ondetti et al.
4,105,776 A    8/1978 Ondetti et al.
4,727,085 A *  2/1988 Shiratsuchi et al. ......... 514/456
7,186,753 B1 * 3/2007 Del Soldato ................ 514/509
7,442,826 B2 * 10/2008 Rivolta et al. ............... 558/482

FOREIGN PATENT DOCUMENTS

WO      01/12584 A2     2/2001
WO      02/094758 A1    11/2002
WO      2005/011646 A2  2/2005

OTHER PUBLICATIONS

Sammakia et al, "2-Formyl-4-pyrrolidinopyridine (FPP): A New Catalyst for the Hydroxyl-Directed Methanolysis of Esters", Journal of the American Chemical Society, 1996, pp. 8967-8968, vol. 118, Boulder, Colorado USA.
Tatsuta K et al, "The First Total Synthesis of Lymphostin" Tetrahedron Letters, Mar. 22, 2004, pp. 2847-2850, vol. 45 No. 13, Elsevier Science Publishers, Amsterdam, NL.
Carini et al, "Nonpeptide Angiotensin II Receptor Antagonists: The Discovery of a Series of N-(Biphenylylmethyl)imidazoles as Potent, Orally Active Antihypertensives", Journal of Medicinal Chemistry, 1991, pp. 2525-2547, vol. 34, American Chemical Society, Wilmington, Delaware USA.

* cited by examiner

Primary Examiner—Susannah Chung
(74) Attorney, Agent, or Firm—Arent Fox LLP

(57) ABSTRACT

The present invention relates to a process for preparing nitrooxy esters, nitrooxy thioesters, nitrooxy carbonates and nitrooxy thiocarbonates of compounds having at least an hydroxyl or thiol functional group, according to the following reaction scheme

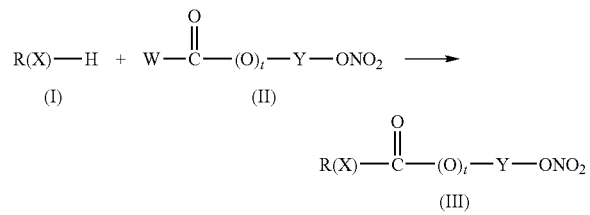

The invention also relates to intermediates useful in said process and to their preparation.

9 Claims, No Drawings

PROCESS FOR PREPARING NITROOXY ESTERS, NITROOXY THIOESTERS NITROOXY CARBONATES AND NITROOXY THIOCARBINATES, INTERMEDIATES USEFUL IN SAID PROCESS AND PREPARATION THEREOF

CROSS-REFERENCE TO RELATED APPLICATION

This application is a National Stage entry of International Application No. PCT/EP2005/050459, filed Feb. 2, 2005, the entire specification and claims of which are incorporated herewith by reference.

The present invention relates to a process for preparing nitrooxy esters, nitrooxy thioesters, nitrooxy carbonates and nitrooxy thiocarbonates of compounds having at least an hydroxyl or thiol functional group, and also to intermediates useful in said process and to their preparation.

In literature, several methods for synthesizing nitrooxy-alkyl/alkylaryl substituted esters from haloalkyl/hydroxy-alkyl carboxylic acids or from nitroxyalkyaryl-carboxylic acids are reported.

WO 01/12584 describes the preparation of 4-(acetylamino) phenyl 4-nitrooxybutanoate The product is obtained by condensation (esterification) of the phenotic group of 4-(acetylamino)phenol with the carboxylic group of 4-bromobutyric acid. The thus obtained 4-bromobutanoate is reacted with silver nitrate.

The principal drawbacks of the above reported synthesis are the use of the silver salts in an amount more than stoichiometric. The use of the silver nitrate in a large amount makes the method expensive and not useful under the point of view of the industrial application. Furthermore the use of a transition metal in the last step of the process, makes difficult the complete removal of the same from the active pharmaceutical product, unless techniques of chromatographic purification are applied.

WO 02/094758 describes a method of synthesis of 21-[4'-(nitrooxyalkyl)benzoate]corticosteroids comprising the reaction of a 21-hydroxyalkylcorticosteroids with a nitrooxyalkyl phenyl carboxylic acid derivatives of formula (I)

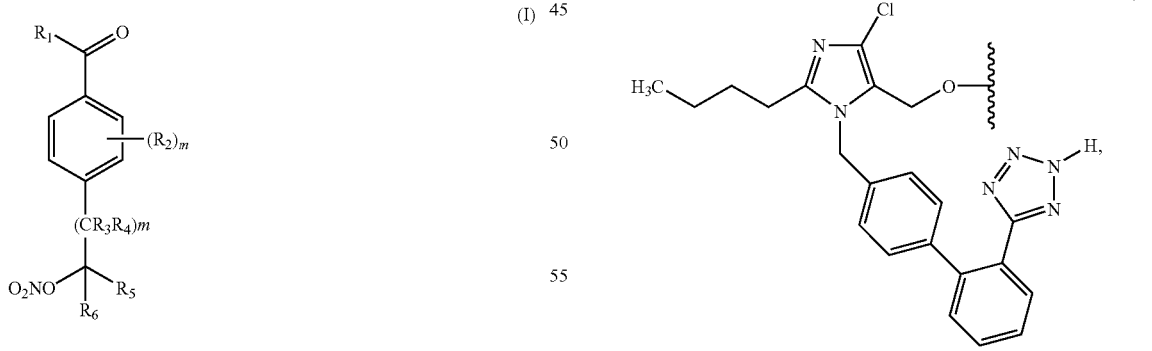

(I)

Wherein R' is OH, an halogen atom or $R^{10}C(O)O$— wherein $R^{10}$ can be an aryl group. The reaction is carried out in the presence of a suitable coupling agent when R' is OH, or in the presence of a suitable base when R' is an halogen atom or the group $R^{10}C(O)O$—.

The present application provides a new method of synthesis which overcomes the drawbacks of the previous method using as intermediates nitrooxy-substituted carboxylic acid and nitrooxy-substituted carbonic acid derivatives in the ready-for-use form of activated esters or activated carbonates. Said intermediates are easily isolable in a substantially pure, easy to react, easy to handle and not explosive.

Moreover, it was surprisingly found that if other functional groups are present in the molecule to be derivatised, as for example a carboxylic group, or a $N^1H$-tetrazole group, they can be unprotected during the reaction.

It was thus an object of the present invention to provide a new process for preparing nitrooxy esters, nitrooxy carbonate, nitrooxy thioesters and nitrooxy thiocarbonates of compounds having at least an hydroxyl or and thiol functional group.

The object of the invention is a process for preparing compounds of general formula (III), according to the following scheme $$R(X)-H + W-\overset{O}{\underset{\|}{C}}-(O)_t-Y-ONO_2 \longrightarrow$$
$$(I) \qquad\qquad (II)$$

$$R(X)-\overset{O}{\underset{\|}{C}}-(O)_t-Y-ONO_2$$
$$(III)$$

comprising reacting:

(a) a compound of formula (I)

(b) a compound of formula (II)

in the presence of dimethylaminopyridine (DMAP) or dimethylaminopyridine and a Lewis acid wherein:

in formula (I), R(X)—, wherein X is O or S, is the radical of a compound selected from the group comprising:

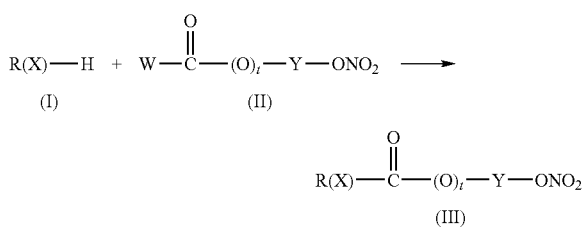

(1c)
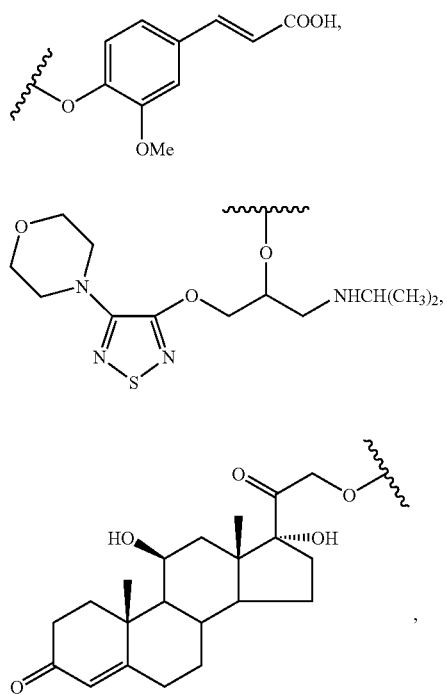
(1d)
(1e)
(1f)
(1g)
(1h)
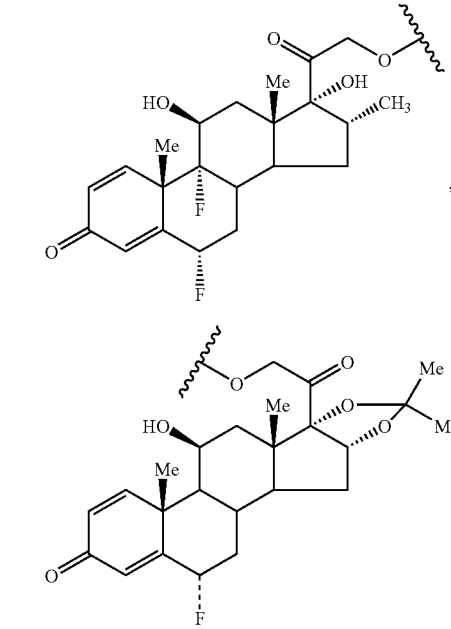
(1i)
(1l)
in formula (II), t is 0 or 1,
W is selected from
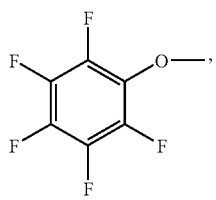
(2a)
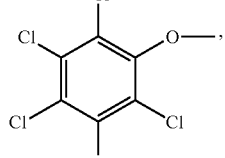
(2b)
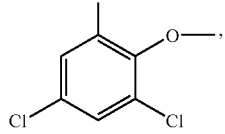
(2c)
(2d)
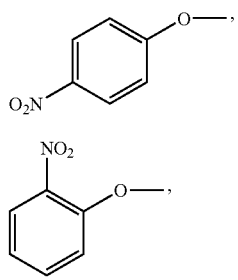
(2e)

-continued (2f)

[Structure: benzene ring with NO2, SO3H substituents and —O— linkage]

(2g)

[Structure: succinimide N—O—CH3]

(2h)

[Structure: N-methoxy pyridine-2-thione]

Y is as defined below;

in formula (III), t, R(X)— and X are as above defined, Y is a bivalent radical having the following meanings:

a)
straight or branched $C_1$-$C_{20}$ alkylene, preferably $C_1$-$C_{10}$ alkylene, more preferably $C_3$-$C_6$ alkylene, being optionally substituted with one or more of the substituents selected from the group consisting of: halogen atoms, hydroxy, —ONO$_2$ or $T_0$, wherein $T_0$ is —OC(O)—($C_1$-$C_{10}$ alkyl)—ONO$_2$ or —O—($C_1$-$C_{10}$ alkyl)—ONO$_2$;

cycloalkylene having from 5 to 7 carbon atoms, the ring being optionally substituted with side chains T, wherein T is straight or branched alkyl with from 1 to 10 carbon atoms, preferably T is $CH_3$;

b)

(2i)

$$—(CH_2)_n \underset{(COOH)_{n2}}{\text{[phenylene]}} (CH_2)_{n1}—$$

wherein n is an integer from 0 to 20, preferably n is 0 or 1, n1 is an integer from 1 to 20, preferably n1 is an integer from 1 to 6, more preferably n1 is 1, n2 is 0 or 1, preferably n2 is 0;

with the proviso that the —ONO$_2$ group is linked to —(CH$_2$)$_{n1}$— group;

c)

(2l)

$$—\underset{R_6}{CH}—(CH_2)_{n3}—X_2—[\underset{R_6}{CH}—(CH_2)_{n4}—X_2]_{n5}—\underset{R_6}{CH}—(CH_2)_{n6}—,$$

d)

(2m)

$$—(CH_2)_{n3}—\underset{R_7}{CH}—X_2—[(CH_2)_{n4}—\underset{R_7}{CH}—X_2]_{n5}—(CH_2)_{n6}—\underset{R_7}{CH}—$$

wherein $X_2$ is O or S, n3, n4 and n6 are integer independently selected from 0 to 20, preferably n4 and n6 are selected from 1 to 5, more preferably n4 and n6 are 1, preferably n3 is selected from 0 to 4, more preferably n3 is 0, n5 is an integer from 0 to 6, preferably from 0 to 4, more preferably n5 is 0, $R_6$ is H, $CH_3$ or nitrooxy group, preferably $R_6$ is H, $R_7$ is $CH_3$ or nitrooxy group;

when Y is selected from the bivalent radicals of the group c) the —ONO$_2$ group is linked to —(CH$_2$)$_{n6}$— group;

when Y is selected from the bivalent radicals of the group d) the —ONO$_2$ group is linked to —CH(R$_7$)— group;

e)

$$—[\underset{R_{10}}{\overset{R_8}{C}}]_{n7}—Y^2—[\underset{R_{11}}{\overset{R_9}{C}}]_{n8}—$$

wherein:

n7 is an integer from 0 to 10;

n8 is an integer from 1 to 10;

$R_8$, $R_9$, $R_{10}$, $R_{11}$ are the same or different, and are H or straight or branched $C_1$-$C_4$ alkyl, preferably $R_8$, $R_9$, $R_{10}$, $R_{11}$ are H;

wherein the —ONO$_2$ group is linked to $$—[\overset{|}{\underset{|}{C}}]_{n8}—$$

wherein n8 is as defined above;

$Y^2$ is an heterocyclic saturated, unsaturated or aromatic 5 or 6 members ring, containing one or more heteroatoms selected from nitrogen, oxygen, sulfur, and is selected from (Y1)

[Structure: pyridine ring]

-continued (Y2) 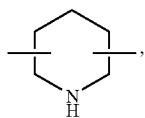

(Y3) 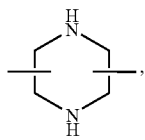

(Y4) 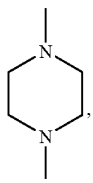

(Y5) 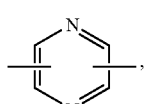

(Y6) 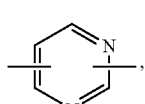

(Y7) 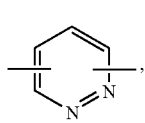

(Y8) 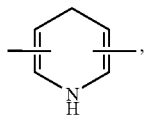

(Y9) 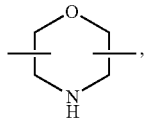

(Y10) 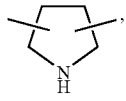

(Y11) 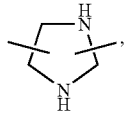

(Y12) 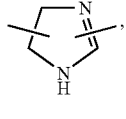

(Y13) 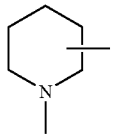

Another object of the present invention are compounds of formula (II)

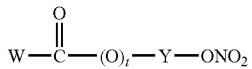
(II)

wherein W, t, Y are as above defined, said compounds are intermediates of the process above reported.

When in formula (I) the R(X) residue is as defined by formula (1a), the compound is known as Losartan;

when in formula (I) the R(X) residue is represented by formula (1b), the compound is known as Captopril;

when in formula (I) the R(X) residue is represented by formula (1c), the compound is known as ferulic acid;

when in formula (I) the R(X) residue is represented by formula (1d) and Z is H, the compound is known as timolol;

when in formula (I) the R(X) residue is represented by formula (1e), the compound is known as hydrocortisone;

when in formula (I) the R(X) residue is represented by formula (1f), the compound is known as dexamethasone;

when in formula (I) the R(X) residue is represented by formula (1g), the compound is known as prednisolone;

when in formula (I) the R(X) residue is represented by formula (1h), the compound is known as budesonide;

when in formula (I) the R(X) residue is represented by formula (1i), the compound is known as flumethasone;

when in formula (I) the R(X) residue is represented by formula (1l), the compound is known as flunisolide;

The compound of formula (I) above reported are commercially available or may be obtained according to processes known in the art; in particular:

Losartan can be prepared as described in D. J. Carini et al., *J. Med. Chem.* 34, 2525 (1991).

Captopril can be prepared as described in M. A. Ondetti, D. W. Cushman, D E 2703828; eider, U.S. Pat. No. 4,046,889 and U.S. Pat. No. 4,105,776 (1977, 1977, 1978

Ferulic acid, Timolol, Prednisolone, Hydrocortisone, dexamethasone, budesonide, flumethasone and flunisolide are commercially available.

The term "$C_1$-$C_{20}$ alkylene" as used herein refers to branched or straight $C_1$-$C_{20}$ saturated hydrocarbon chain that results from the removal of two hydrogen atoms from an acyclic saturated hydrocarbon, preferably having from 1 to 10 carbon atoms such as —$CH_2$—, —$CH_2$—$CH_2$—, —$(CH_2)_3$—, —$(CH_2)_4$—, —$(CH_2)_5$—, —$(CH_2)_6$— and the like.

The term "$C_1$-$C_{10}$ alkyl" as used herein refers to branched or straight chain alkyl groups comprising one to ten carbon atoms, including methyl, ethyl, n-propyl, isopropyl, n-butyl, isobutyl, t-butyl, n-pentyl, n-hexyl, n-octyl and the like.

The term "cycloalkylene" as used herein refers to ring having from 5 to 7 carbon atoms including, but not limited to, cyclopentylene, cyclohexylene optionally substituted with side chains such as straight or branched ($C_1$-$C_{10}$)-alkyl, preferably $CH_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

In one aspect of the invention and as reported above in the general reaction scheme, the reaction between the compound of formula (I) and the nitrooxyderivative of formula (II) is carried out in the presence of dimethylaminopyridine (DMAP) in at least an equimolar amount respect to compound (II).

The molar ratio of compounds of formulas (I):(II) is from 1 to 0.5.

The molar ratio (II):DMAP is 1.

When in the structure of compound (I) of formula R(X)H a free carboxylic acid group or a 1N—H tetrazole group is present an additional equimolar amount of inorganic or organic bases such as DMAP, TEA, pyridine, DIPEA tributylphosphine has added.

The reaction is typically carried out in a temperature range from about −15° C. to about 100° C., preferably from −5° C. to 40° C.

Generally, the reaction is carried out in an organic solvent, generally an aprotic solvent, such as pyridine, methylene chloride, or chloroform or dipolar solvents such as acetone, tetrahydrofurane, dimethylformamide (DMF), N-methylpyrrolidone, sulfolane, acetonitrile or in a mixture thereof, depending on the solubility of the compounds involved in the reaction; the preferred solvent are methylene chloride, DMF, a mixture of methylene chloride and THF, or a of mixture of methylene chloride and DMF.

In another embodiment the reaction between the compound of formula (I) and the nitrooxyderivative of formula (II) is carried out in the presence of a catalytic amount of a Lewis acid catalyst such as bismuth triflate, scandium triflate, and in the presence of at least an equimolar amount of DMAP respect to compound (II). The preferred Lewis acid catalyst is Scandium triflate.

The molar ratio of compounds of formulas (I):(II) is from 1 to 0.5.

Preferably the molar ratio (II):DMAP is 1.

The molar ratio (II):DMAP:Sc(OTf)$_3$ is 1:1:0.1.

When in the structure of compound (I) of formula R(X)H a free carboxylic acid group or a 1N—H tetrazole group is present an additional equimolar amount of inorganic or organic bases such as DMAP, TEA, pyridine, DIPEA tributylphosphine has added. The preferred base is DMAP. Preferably when the compound of formula (I) has an acidic unprotected function and when in compound of formula (II), Y is the group of formula (21) wherein n1 is 1 (i.e. Y is a benzylic nitrate) the reaction is always carried out with Sc(OTf)$_3$ in the presence of an excess of DMAP.

The reaction is typically carried out in a temperature range from about −15° C. to about 100° C., preferably from −5° C. to 40° C., 1A) The compounds of formula (II) as above defined are obtained as below reported.

The compounds of formula (II) wherein W and Y are as above defined and t is 1, are obtained by reacting:

compounds of formula (IVa)

   (IVa)

with a compounds of formula (V)

   (V)

wherein W is as above defined, in the presence of DMAP

The molar ratio of (V):(IVa):DMAP is 1.2:1:2;

The reaction is carried out in an organic solvent, generally an aprotic solvent, such as pyridine, methylene chloride, or chloroform or dipolar solvents such as acetone, tetrahydrofurane, dimethylformamide (DMF), N-methylpyrrolidone, sulfolane, acetonitrile or in a mixture thereof.

The reaction is typically carried out in a temperature range from about −15° C. to about 100° C., preferably from −5° C. to 40° C.

2A.1) The compounds of formula (V) as above defined are commercially available or are obtained by reacting compounds of formula (VI)

   (VI)

with phosgene or triphosgene in the presence of a base such as pyridine, TEA or DIPEA in methylene chloride, or THF or DMF or a mixture thereof.

The reaction is typically carried out in a temperature range from about −15° C. to about 100° C., preferably from 0° C. to 40° C.

2B) Alternatively the compounds of formula (II) wherein W and Y are as above defined and t is 1, are obtained by reacting:

compounds of formula (IVa)

   (IVa)

with a compounds of formula (V)

   (V)

wherein W is as above defined, in the presence of a catalytic amount of a Lewis acid catalyst such as bismuth triflate, scandium triflate, and of at least an equimolar amount of DMAP respect to compound (V).

The molar ratio (V):(IVa):Sc(OTf)$_3$:DMAP is 1.2:1:0.12:2.

The reaction is carried out in an organic solvent, generally an aprotic solvent, such as pyridine, methylene chloride, or chloroform or dipolar solvents such as acetone, tetrahydrofurane, dimethylformamide (DMF), N-methylpyrrolidone, sulfolane, acetonitrile or in a mixture thereof.

The reaction is typically carried out in a temperature range from about −15° C. to about 100° C., preferably from −5° C. to 40° C.

2B.1) The compounds of formula (V) as above defined are commercially available or are obtained using method described in 2A.1).

2B.2) The compounds of formula (IVa)

   (IVa)

wherein Y is as above defined, are obtained by reacting the commercially available compounds of formula HO—Y-Hal (IVa') wherein Hal is an halogen atom, and Y is as above defined, with AgNO$_3$ in a suitable organic solvent such as acetonitrile or tetrahydrofuran (THF) under nitrogen in the dark at temperatures range between 20°-80° C.; alternatively the reaction with AgNO$_3$ can be performed under microwave irradiation in solvents such acetonitrile or THF at temperatures in the range between about 100-180° C. for time range about 1-60 min.

The compounds of formula (IVa') are commercially available or can be obtained by method well known in the literature;

3A) The compounds of formula (II) wherein W and Y are as above defined and t is 0, are obtained by reacting:

compounds of formula (IVb)

   (IVb)

wherein Y is as above defined, with a compound of formula (VI)

   (VI)

Wherein W is as above defined, in the presence of a condensing agent such as DCC, EDAC.HCl.

The reaction is carried out in dichloromethane, THF, DMF or other solvent.

4A) Alternatively, compounds of formula (II) as above defined are obtained by reacting:

a compound of formula (VII)

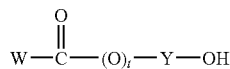

(VII)

by in situ derivatization and nitration with triflic anhydride/quaternary ammonium nitrates salts in the presence of excess of a base such as DMAP, pyridine, TEA or DIPEA.

Preferred quaternary ammonium nitrates is tetraethyl ammonium nitrate.

The reaction is carried out at a temperature range from about −50° C. to 100° C. Preferably in a temperature range from −50° C. to 40° C.

The reaction is carried out in an organic solvent, generally in a solvent selected from acetone, tetrahydrofurane, dimethylformamide, N-methylpyrrolidone, sulfolane, acetonitrile, methylene chloride.

Preferred solvent are dichloromethane or dichloro methane/DMF.

The molar ratio (VII):triflic anhydride:tetraalkylammonium nitrate is 1:2:2 1

4A.1) Compounds of formula (VII) where t is 1 can be obtained from compounds (V) and commercially available compounds of formula (VIIa)

HO—Y—OH (VIIa)

using the same procedure described in 2B) using the compound (VIIa) instead of compounds (IVa).

4A.2) Compounds of formula (VII) where t is 0 are obtained using method described for the preparation of compounds (II) reacting (VI) with commercially available compounds of formula (VIIb)

HO—Y—COOH (VIIb)

in the presence of condensing agents as DCC or EDAC.HCl as well known in the art.

5A) Alternatively, compounds of formula (II) as above defined are obtained by reacting:

a compound of formula (VII)

(VII)

with sulfonitric mixture according to the method known in the art.

The compounds of formula (II) may be isolated and stored at −20° C. degrees.

5A.1) Compounds of formula (VII) where t is 1 are obtained as described in 4A.1)

5A.2) Compounds of formula (VII) where t is 0 are obtained using method described 4A.2).

6A) Alternatively, compounds of formula (II) as above defined are obtained by reacting:

compounds of formula (VIII)

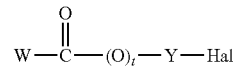

(VIII)

wherein Hal is an halogen atom selected from Cl, Br, I, Y and t are as above defined;

with nitrating agents such as alkaline metal nitrates, quaternary ammonium nitrates, quaternary phosphonium salts and $AgNO_3$, $Zn(NO_3)_2 6H_2O$. Preferably $AgNO_3$ is used.

The molar ratio (VIII)/nitrating agent is from 1:2 to 1:10, preferably the molar ratio is 1:3.

The reaction is carried out in a temperature range from about 0° C. to about 150° C.

The reaction is carried out in solvent such as acetonitrile. High temperature are obtained performing the reaction in a microwave apparatus.

6A.1) Compounds of formula VIII where W and Y are as above described and t is 1 are obtained by reacting compounds of formula (VI) with commercially available compound of formula (VIIIa)

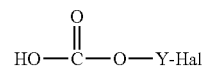

(VIIIa)

in dichloromethane, THF, DMF or other, in the presence of a base such as Pyridine, TEA, DIPEA and DMAP as known in the art.

6A.2) Compounds of formula VIII where W and Y are as above described and t 0 can be obtained reacting compounds of formula (VI) with commercially available compound of formula (VIIIb)

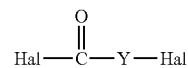

(VIIIb)

in dichloromethane, THF, DMF or other, in the presence of a condensing agent as DCC or EDAC.HCl and DMAP according to method known in the art.

The following examples are to further illustrate the invention without limiting it.

EXAMPLE 1

Two-step process synthesis of 4-(Nitrooxy)butanoic acid 4-acetamidophenyl ester of formula (IIIa)

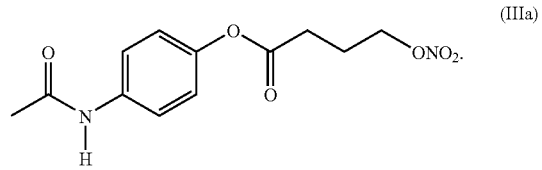

(IIIa)

Step 1: synthesis of 4-(Nitrooxy)butanoic acid pentafluorophenyl ester (Preparation 1)

To a solution of 4-bromobutyric acid (0.91 g, 5.4 mmol), pentafluorophenol (1.00 g, 5.4 mmol) and DMAP (0.13 g, 1.1 mmol) in $CH_2Cl_2$ (10 ml) cooled to 0° C. under nitrogen, N,N-dicyclohexylcarbodiimide (1.70 g, 8.1 mmol) was added in portions. After 1 h the reaction was slowly warmed to room temperature and stirred for 5 hours. The dicyclohexylurea was filtered off and the mother liquor was concentrated and purified by flash chromatography (n-Hexane/EtOAc 98:2) affording 4-bromobutyric acid pentafluorophenyl ester as a colourless oil (1.40 g, 78%). A mixture of 4-bromobutyric acid pentafluorophenyl ester (0.65 g, 1.9 mmol) and $AgNO_3$ (0.83 g, 4.9 mmol) in $CH_3CN$ (8 ml) was warmed at 70° C. for 20 minutes at the microwave. The formed salts were filtered off, the solvent was concentrated and the residue purified by flash chromatography (n-Hexane/EtOAc 95:5) affording 4-nitrooxybutyric acid pentafluorophenyl ester as a clear oil (0.38 g, 62%).

$^1$H NMR ($CDCl_3$) δ: 4.60 (2H, t), 2.86 (2H, t), 2.23 (2H, m).

Step 1: synthesis of 4-(Nitrooxy)butanoic acid pentafluorophenyl ester (Preparation 2)

To a mixture of pentafluorophenol (3.3 g, 17.96 mmol), 4-bromobutanoic acid (3.0 g, 17.96 mmol) and DMAP (0.440 g, 3.59 mmol) in $CH_2Cl_2$ (30 ml), cooled to 0° C., EDAC.HCl (5.2 g, 26.94 mmol) was added in portion. The mixture was then stirred at 0° C. for 30 minutes. Then it was gradually warmed to room temperature and stirred for 480 minutes. Then the mixture was diluted with $NaH_2PO_4$ aqueous (5%, 50 ml) and acidified with HCl 1N to pH 3-4. The organic phase was separated and the aqueous phase was extracted with $CH_2Cl_2$ (2×50 ml). The organic phase washed with brine, dried over $Na_2SO_4$ and evaporated to give an oil that was purified by flash chromatography (n-Hexane/EtOAc 98:2) to yield 4-bromobutanoic acid pentafluorophenyl ester (5.2 g, 86%) as a colorless oil.

A mixture of 4-bromobutanoic acid pentafluorophenyl ester (5.2 g, 15.61 mmol) and $AgNO_3$ (6.6 g, 39.03 mmol) in $CH_3CN$ was heated at 60° C. for 300 minutes under nitrogen, in the dark.

Then the mixture was cooled, concentrated and diluted with EtOAc. The silver salts were filtered off, the solvent evaporated. After flash chromatography purification (n-Hexane/EtOAc 95:5) 4-(nitrooxy)butanoic acid pentafluorophenyl ester (3.9 g, 80%) was obtained as a colorless oil.

$^1$H NMR ($CDCl_3$) δ: 4.60 (2H, t), 2.86 (2H, t), 2.23 (2H, m).

Step 2: synthesis of 4-(Nitrooxy)butanoic acid 4-acetamidophenyl ester of formula (IIIa)

To a solution of 4-acetamidophenol (Paracetamol) (0.96 g, 6.30 mmol) TEA (0.64 g, 6.3 mmol) and DMAP (0.77 g, 6.3 mmol) in $CH_2Cl_2$/THF (9:1, 30 ml) kept at 0° C., under stirring and under nitrogen atmosphere, a solution of 4-(nitrooxy)butanoic acid pentafluorophenyl ester (2.0 g, 6.30 mmol) (Preparation 2) in $CH_2Cl_2$ (10 ml) was added. The resulting solution was kept under stirring for further 240 minutes at room temperature. The reaction mixture was poured in a pH 3 buffer solution (about 50 ml), acidified with HCl 1 N to pH 3-4 and extracted with $CH_2Cl_2$ (2×50 ml). The organic phase washed with brine (100 ml), dried on sodium sulfate and evaporated under vacuum. Purification by Flash chromatography of the residue (n-hexane/AcOEt 1:1) gave the title compound as a white solid (1.52 g, 84%). M.p., NMR and HPLC analysis were consistent with data reported in the literature.

$^1$HNMR ($CDCl_3$) δ: 7.55 (1H, s); 7.49 (2H, d); 7.02 (2H, d); 4.58 (2H, t); 2.71 (2H, t); 2.19 (2H, m); 2.14 (3H, s).

EXAMPLE 2

Two-steps process synthesis of 2-butyl-4-chloro-1-[[2'-(1H-tetrazol-5-yl)[1,1'-biphenyl]-4-yl]methyl]-5-[(3-(nitrooxy) propyl)carbonyloxy]methyl-1H-imidazole of formula (IIIb)

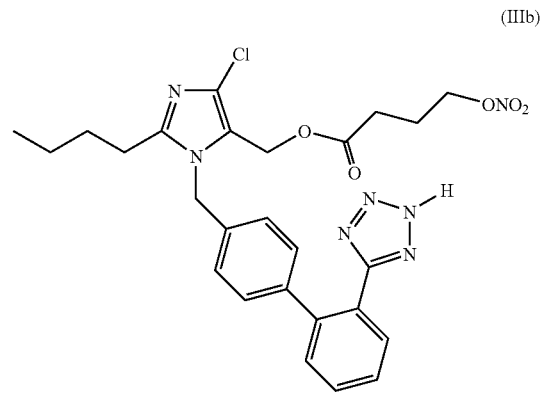

(IIIb)

Step 1: synthesis of 4-(Nitrooxy)butanoic acid pentafluorophenyl ester

The compound was synthesized using the method described in (Preparation 2)

Step 2: synthesis of 2-butyl-4-chloro-1-[[2'-(1H-tetrazol-5-yl)[1,1'-biphenyl]-4-yl]methyl]-5-[(3-(nitrooxy) propyl)carbonyloxy]methyl-1H-imidazole; 4-(nitrooxy) butanoic acid Using the same procedure described in Example 1 but starting from 2-butyl-4-chloro-1-[[2'-(1H-tetrazol-5-yl)[1,1'-biphenyl]-4-yl]methyl]-1H-imidazole-5-methanol (Losartan)(2.13 g, 5.04 mmol) and 4-(nitrooxy)butanoic acid pentafluorophenyl ester (1.59 g, 5.04 mmol) TEA (0.7 ml, 5.04 mmol), DMAP (0.615 g, 5.04 mmol) and using DMF as solvent. Then the mixture was diluted with buffer solution (pH=3); the pH was adjusted to 2-3 and the mixture was extracted with EtOAc. The organic phase washed with brine, dried over $Na_2SO_4$ and evaporated. The residue was purified with Flash chromatography of the residue ($CH_2Cl_2$/MeOH 98:2) and the title compound was obtained as a white solid (1.48 g, 53%).

m.p. 66-68° C.

$^1$H NMR ($CDCl_3$) δ: 7.85 (1H, d), 7.58 (2H, m), 7.42 (1H, d), 7.11 (2H, d), 6.79 (2H, d), 5.15 (2H, s), 4.94 (2H, s), 4.42 (2H, t), 2.53 (2H, t); 2.21 (2H, t), 1.93 (2H, m), 1.56 (2H, m), 1.29 (2H, m), 0.85 (3H, t).

EXAMPLE 3

Two-steps process synthesis of 2-butyl-4-chloro-1-[[2'-(1H-tetrazol-5-yl)[1,1'-biphenyl]-4-yl]methyl]-5-[(3-(nitrooxy) propyl)carbonyloxy]methyl-1H-imidazole of formula (IIIb)

Step 1: synthesis of 4-(Nitrooxy)butanoic acid pentafluorophenyl ester

The compound was synthesized using the method described in (Preparation 1)

Step 2: synthesis of 2-butyl-4-chloro-1-[[2'-(1H-tetrazol-5-yl)[1,1'-biphenyl]-4-yl]methyl]-5-[(3-(nitrooxy)propyl) carbonyloxy]methyl-1H-imidazole of formula (IIIb)

To a solution of 2-butyl-4-chloro-1-[[2'-(1H-tetrazol-5-yl)[1,1'-biphenyl]-4-yl]methyl]-1H-imidazole-5-methanol (0.48 g, 1.1 mmol), TEA (0.16 ml, 1.1 mmol) and DMAP (0.14 mg, 1.1 mmol) in DMF (3 ml), cooled to 0° C., a solution of 4-nitrooxybutyric acid pentafluorophenyl ester (0.36 g, 1.1 mmol) in DMF (3 ml) was added. The reaction was slowly warmed to room temperature and stirred for 3 hours. Then the solvent was evaporated under reduced pressure. The residue was dissolved in EtOAc (10 ml) and washed with a buffer solution (pH=3) then with brine. The organic layer was dried over $Na_2SO_4$, concentrated and purified by flash chromatography ($CH_2Cl_2$/MeOH 98:2) to afford the title compound (0.41 g, 66%).

EXAMPLE 4

Two-steps process synthesis of 2-butyl-4-chloro-1-[[2'-(1H-tetrazol-5-yl)[1,1'-biphenyl]-4-yl]methyl]-5-[(4-(nitrooxy) butyl)carbonyloxy]methyl-1H-imidazole of formula (IIIc);

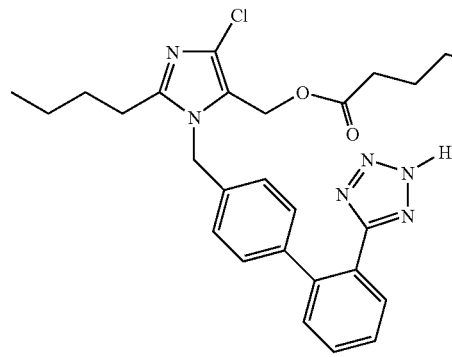

(IIIc)

Step 1: synthesis of 5-(nitrooxy)pentanoic acid pentafluorophenyl ester (preparation 3)

Starting from 5-bromopentanoic acid (1.0 g, 5.52 mmol) and pentafluorophenol (1.0 g, 5.52 mmol), applying the same procedure described in Preparation 2, 5-bromopentanoic acid pentafluorophenyl ester (1.5 g, 78%) was obtained as a colorless oil.

From 5-bromopentanoic acid pentafluorophenyl ester (1.5 g, 4.32 mmol) and $AgNO_3$ (1.8 g, 10.80 mmol), heating to reflux and applying the same procedure described in Preparation 2, after flash chromatography purification (n-Hexane/EtOAc 98:2) 5-(nitrooxy)pentanoic acid pentafluorophenyl ester (0.72 g, 50%) was obtained as a pale yellow oil.

$^1$H NMR (CDCl$_3$) δ:4.53 (2H, t), 2.77 (2H, t), 2.00-1.85 (4H, m).

Step 2: synthesis of 2-butyl-4-chloro-1-[[2'-(1H-tetrazol-5-yl)[1,1'-biphenyl]-4-yl]methyl]-5-[(4-(nitrooxy)butyl) carbonyloxy]methyl-1H-imidazole Using the same procedure described in Example 1 but starting from 2-Butyl-4-chloro-1-[[2'-(1H-tetrazol-5-yl)[1,1'-biphenyl]-4-yl]methyl]-1H-imidazole-5-methanol (Losartan) (0.93 g, 2.19 mmol) and 5-(nitrooxy)pentanoic acid pentafluorophenyl ester (0.72 g, 2.19 mmol) TEA (0.30 ml, 2.19 mmol), DMAP (0.27 g, 2.19 mmol) after purification with Flash chromatography of the residue ($CH_2Cl_2$/MeOH 98:2) the title compound (0.72 g, 60%) was obtained as a white foam.

$^1$H NMR (CDCl$_3$) δ: 7.72-7.48 (4H, m); 7.10 (2H, d); 6.94 (2H, d); 5.24 (2H, s); 5.00 (2H, s); 4.44 (2H, t); 2.10 (2H, t); 1.57-1.44 (6H, m); 1.29 (4H, m); 0.83 (3H, t).

EXAMPLE 5

Two-steps process synthesis of 1-[(2S)-3-[(3-(nitrooxy) propyl)carbonylthio]-2-methyl-1-oxopropyl]-L-proline of formula (IIId)

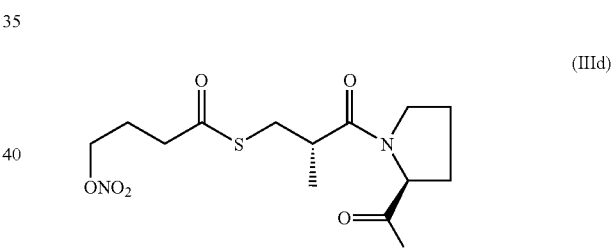

(IIId)

Step 1: synthesis of 4-(Nitrooxy)butanoic acid pentafluoro phenyl ester

The compound was synthesized using the method described in (Preparation 2)

Step 2: synthesis of 1-[(2S)-3-[(3-(nitrooxy)propyl) carbonylthio]-2-methyl-1-oxopropyl]-L-proline Using the same procedure described in Example 1 but starting from 1-[(2S)-3-mercapto-2-methyl-1-oxopropyl]-L-proline (Captopril)(0.41 g, 1.9 mmol), 4-(nitrooxy)butanoic acid pentafluorophenyl ester (0.60 g, 1.9 mmol) TEA (0.26 ml, 1.9 mmol) and DMAP (0.23 g, 1.9 mmol) after purification with Flash chromatography of the residue ($CH_2Cl_2$/Acetone 80:20) the title compound (0.140 g, 20%) was obtained as a white foam.

$^1$H NMR (CDCl$_3$) δ: 4.61 (1H, m); 4.51 (2H, t); 3.61 (2H, m); 3.15 (1H, dd); 3.02 (1H, dd); 2.72 (2H, t); 2.39 (1H, m); 2.08 (5H, m); 1.27 (3H, d).

EXAMPLE 6

Synthesis of 2-butyl-4-chloro-1-[[2'-(1H-tetrazol-5-yl) [1,1'-biphenyl]-4-yl]methyl]-5-[[((4-(nitrooxy)methyl)phenyl]carbonyloxy]methyl-1H-imidazole of formula (IIIe)

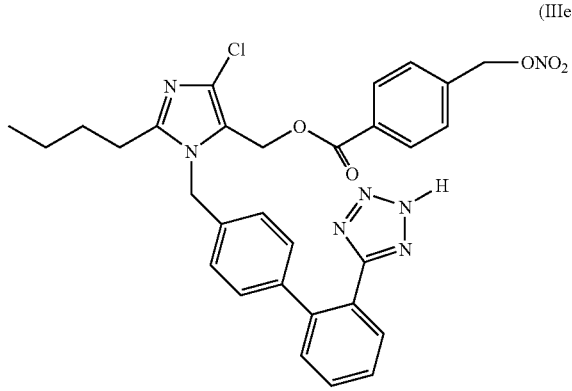

(IIIe)

Step 1: synthesis of [4-(nitrooxy)methyl]benzoic acid pentafluorophenyl ester (preparation 4)

Starting from 4-(bromomethyl)benzoic acid (5.0 g, 23.25 mmol) and pentafluorophenol (4.3 g, 23.25 mmol), applying the same procedure described in Preparation 2, 4-(bromomethyl)benzoic acid pentafluorophenyl ester (5.0 g, 56%) was obtained as an off white solid.

From 4-(bromomethyl)benzoic acid pentafluorophenyl ester (5.0 g, 13.12 mmol) and AgNO₃ (5.6 g, 32.80 mmol), heating to reflux and applying the same procedure described in Preparation 2, after flash chromatography purification (n-Hexane/EtOAc 95:5) [4-(nitrooxy)methyl]benzoic acid pentafluorophenyl ester (4.2 g, 88%) was obtained as a white solid.

m.p. 75-76° C.

$^1$H NMR (CDCl$_3$) δ: 8.26 (2H, d), 7.60 (2H, d), 5.55 (2H, s).

Step 2: synthesis of 2-butyl-4-chloro-1-[[2'-(1H-tetrazol-5-yl) [1,1'-biphenyl]-4-yl]methyl]-5-[[((4-(nitrooxy)methyl)phenyl]carbonyloxy]methyl-1H-imidazole To a solution of 2-butyl-4-chloro-1-[[2'-(1H-tetrazol-5-yl) [1,1'-biphenyl]-4-yl]methyl]-1H-imidazole-5-methanol (Losartan) (3.1 g, 7.27 mmol) Sc(OTf)$_3$ (0.3 g, 0.61 mmol) and DMAP (1.5 g, 12.12 mmol) in CH$_2$Cl$_2$ (25 ml) kept at −5° C., under stirring and under nitrogen atmosphere, a solution of [4-(nitrooxy)methyl]benzoic acid pentafluoro phenyl ester (2.2 g, 6.06 mmol) in CH$_2$Cl$_2$ (5 ml) was added. The resulting solution was kept under stirring for further 16 hrs at room temperature. The reaction mixture was poured into a pH 3 buffer solution (about 50 ml), acidified with HCl 1 N to pH 3-4 and extracted with CH$_2$Cl$_2$ (2×50 ml). The organic phase was dried on sodium sulfate and evaporated.

After purification with Flash chromatography of the residue (CH$_2$Cl$_2$/MeOH 98:2) the title compound was obtained as a white solid (1.70 g, 47%).

m.p. 155

$^1$H NMR (DMSO) δ: 7.73-7.56 (5H, m); 7.47 (2H, d); 7.24 (1H, d); 7.00 (4H, m); 5.60 (2H, s); 5.36 (2H, s); 5.27 (2H, s); 2.56 (2H, t); 1.53 (2H, m); 1.28 (2H, m); 0.82 (3H, t).

EXAMPLE 7

Synthesis of 4-(nitrooxy)butyl pentafluorophenyl carbonate

To a solution of pentafluorophenol (1 g, 5.43 mmol) and TEA (0.91 ml, 6.52 mmol) in CHCl$_3$ (8 ml), cooled to 0° C. and under nitrogen, a solution of 4-chlorobutyl chloroformate (0.76 ml, 5.43 mmol) in CHCl$_3$ (1 ml) was dropped into. The mixture was allowed to warm to room temperature and stirred for 480 minutes. Then it was diluted with aqueous KHSO$_4$ (2%), the two phases were separated and the organic phase was dried and evaporated yielding 4-chlorobutyl pentafluorophenyl carbonate (1.69 g, 98%) as a colorless oil that was used without further purification.

A mixture of 4-chlorobutyl pentafluorophenyl carbonate (1.69 g, 5.3 mmol) and NaI (7.99 g, 53.3 mmol) in CH$_3$CN (20 ml) was refluxed under nitrogen for 960 minutes. Then the solvent was evaporated and the residue taken up with CH$_2$Cl$_2$ and washed with water (2×50 ml). The organic phase was then dried and evaporated yielding 4-iodobutyl pentafluorophenyl carbonate (1.95 g, 90%) as a yellow oil that was used without further purification.

A mixture of 4-iodobutyl pentafluorophenyl carbonate (1.95 g, 4.75 mmol) and AgNO$_3$ (14.6 mmol) was stirred under nitrogen in the dark at room temperature for 24 hrs.

Then the silver salts were filtered and, following the same procedure already described (Preparation 2), after flash chromatography purification (n-Hexane/EtOAc 95:5) 4-(nitrooxy)butyl pentafluorophenyl carbonate (0.99 g, 60%) was obtained as a colorless oil.

$^1$H NMR (CDCl$_3$) δ: 4.51 (2H, t); 4.15 (2H, t); 1.94 (4H, m)

EXAMPLE 8

Synthesis of [3-(Nitrooxy)methyl]phenyl 4-nitrophenyl carbonate

Following the same procedure described in Preparation 3, but starting from 3-(bromomethyl)phenol (9.3 g, 49.6 mmol) and 4-nitrophenyl chloroformate (10 g, 49.6 mmol) after purification of the residue by flash chromatography (n-Hexane/EtOAc 85:15) 3-(bromomethyl)phenyl 4-nitrophenyl carbonate (3.7 g, 21%) was obtained as white solid.

A mixture of 3-(bromomethyl)phenyl 4-nitrophenyl carbonate (3.6 g, 10.2 mmol) and AgNO$_3$ (8.66 g, 51 mmol) in CH$_3$CN under nitrogen, in the dark, was heated to 60° C. for 48 hrs. Then applying the same procedure described in Preparation 2, after Flash chromatography purification [3-(nitrooxy)methyl]phenyl 4-nitrophenyl carbonate (3.3 g, 96%) was obtained as a pale yellow solid.

$^1$H NMR (CDCl$_3$) δ: 8.33 (2H, d); 7.49 (2H, d); 7.49-7.20 (4H, m); 5.58 (2H, s).

EXAMPLE 9

Synthesis of 4-(Nitrooxy)butanoic acid N-succinimidyl ester

To a mixture of N-hydroxysuccinimide (3.3 g, 28.74 mmol), 4-bromobutanoic acid (4.0 g, 23.95 nmol) and DMAP (0.59 g, 4.82 mmol) in CH$_2$Cl$_2$ (40 ml), cooled to 0° C., DCC (7.4 g, 35.93 mmol) was added in portion. The mixture was then stirred at 0° C. for 30 minutes. Then it was gradually warmed to room temperature and stirred for 480 minutes. Then the mixture was diluted with EtOAc (40 ml) and the solid was filtered off and the solvent was evaporated. The residue was taken with EtOAc and the organic phase washed with brine, dried over $Na_2SO_4$ and evaporated. The residue was purified by Flash chromatography (n-Hexane:EtOAc 70:30) yielding 4-bromobutanoic acid N-succinimidyl ester (3.0 g, 48%) as a white solid.

A solution of 4-bromobutanoic acid N-succinimidyl ester (1.8 g, 6.82 mmol) and $AgNO_3$ (2.9 g, 17.04 mmol) in $CH_3CN$ (18 ml) was heated to 70° C. for 18 minutes in a microwave apparatus (Creator®, Biotage). Then the mixture was cooled, diluted with EtOAc and the silver salts were filtered off and the solvent evaporated to give 4-(nitrooxy)butanoic acid N-succinimidyl ester (1.4 g, 83%).

$^1$H NMR (CDCl$_3$) δ: 4.59 (2H, t); 2.87 (4H, m); 2.79 (2H, t); 2.21 (2H, m).

The invention claimed is:

1. A process for preparing compounds of general formula (III)

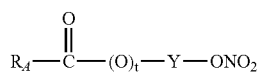
(III)

comprising reacting:
(a) a compound of formula (I)

$R_A$—H, and  (I)

(b) a compound of formula (II)

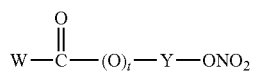
(II)

in the presence of dimethylaminopyridine (DMAP), or dimethylaminopyridine (DMAP) and a Lewis acid selected from the group consisting of bismuth triflate and scandium triflate, wherein:
in formula (I), $R_A$ is selected from the group consisting of:

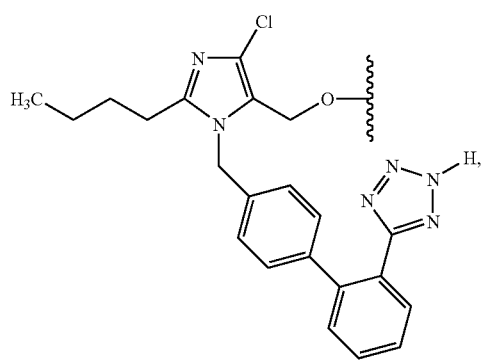
(1a)

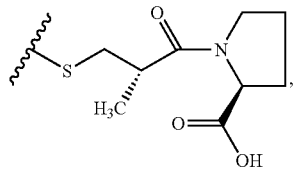
(1b)

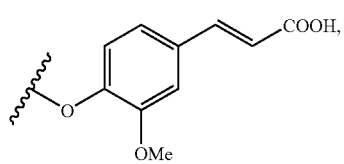
(1c)

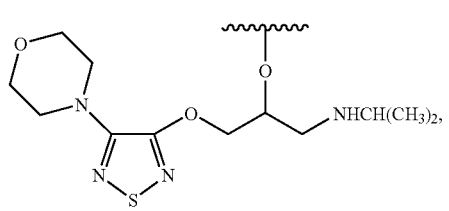
(1d)

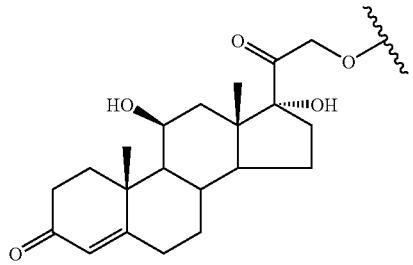
(1e)

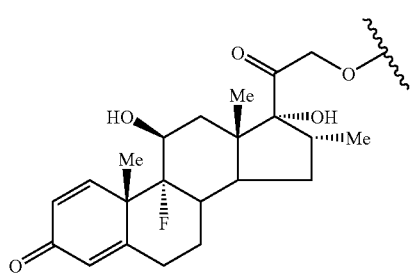
(1f)

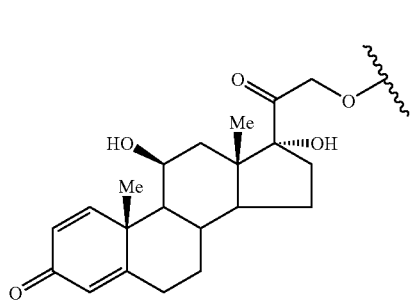
(1g)

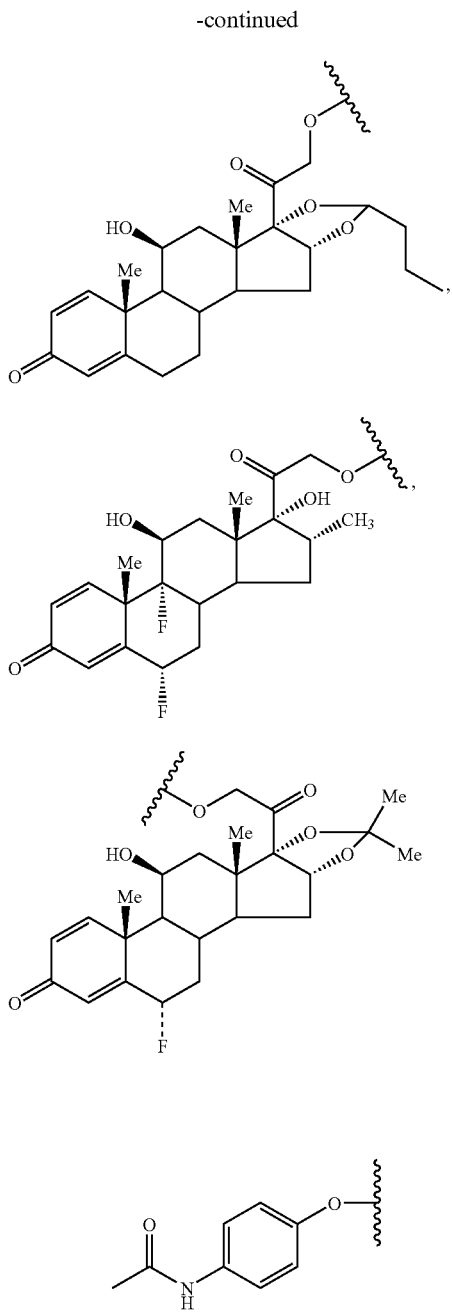

in formula (II), t is 0 or 1
W is selected from the group consisting of:

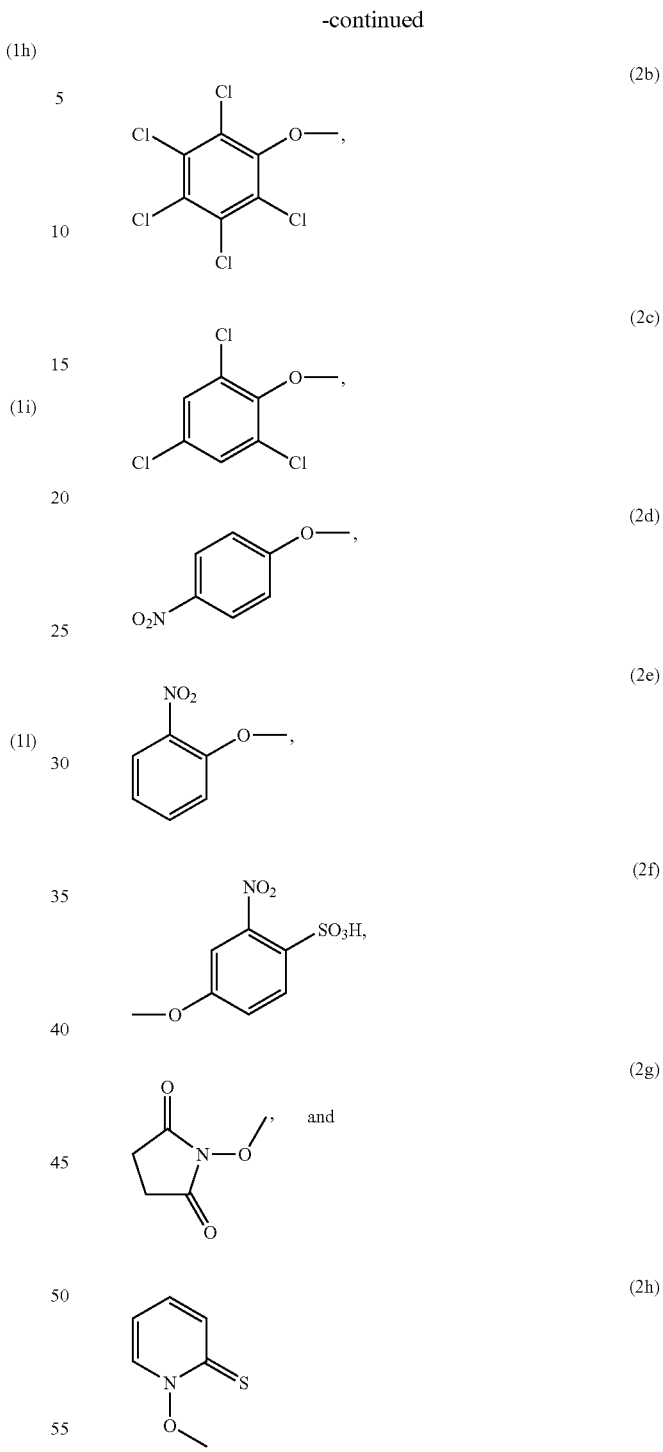

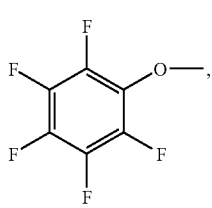

Y is a bivalent radical having the following meanings:
  a) a straight or branched $C_1$-$C_{20}$ alkylene, optionally substituted with one or more of the substituents selected from the group consisting of: halogen atoms, hydroxy, —$ONO_2$ and $T_0$, wherein $T_0$ is —OC(O)—($C_1$-$C_{10}$ alkyl)-$ONO_2$ or —O—($C_1$-$C_{10}$ alkyl)-$ONO_2$; or a cycloalkylene having from 5 to 7 carbon atoms, wherein the cycloalkylene is optionally substituted with T, wherein T is a straight or branched alkyl with from 1 to 10 carbon atoms; or b)

(2i)

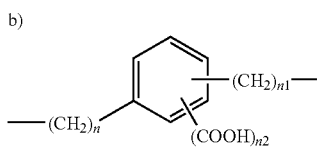

wherein:
n is an integer from 0 to 20,
n1 is an integer from 1 to 20,
n2 is 0 or 1;
wherein the —ONO$_2$ group is linked to —(CH$_2$)$_{n1}$— group;

c)

(2l)

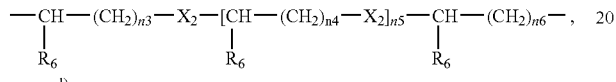

d)

(2m)

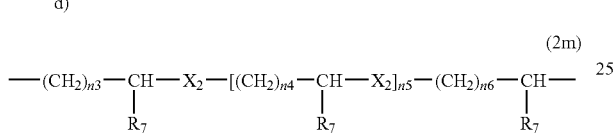

wherein the —ONO$_2$ group is linked to the —(CH$_2$)$_{n6}$— group;
wherein the —ONO$_2$ group is linked to the —(CH(R$_7$)— group; and
wherein X$_2$ is O or S,
n3, n4 and n6 are integer independently selected from 0 to 20,
n5 is an integer from 0 to 6,
R$_6$ is H, CH$_3$ or nitrooxy group,
R$_7$ is CH$_3$ or nitrooxy group, e)

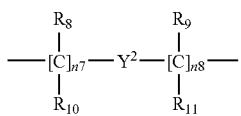

wherein:
n7 is an integer from 0 to 10;
n8 is an integer from 1 to 10;
R$_8$ R$_9$, R$_{10}$, R$_{11}$ are the same or different, and are H or straight or branched C$_1$-C$_4$ alkyl; wherein the —ONO$_2$ group is linked to

wherein n8 is as defined above
Y$^2$ is selected from the group consisting of:

(Y1)

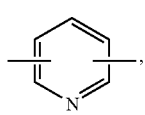

-continued (Y2)

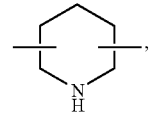

(Y3)

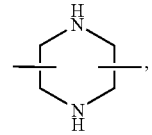

(Y4)

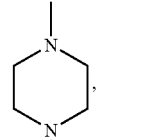

(Y5)

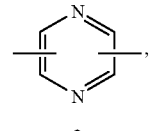

(Y6)

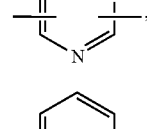

(Y7)

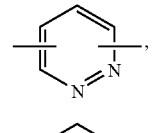

(Y8)

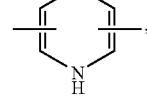

(Y9)

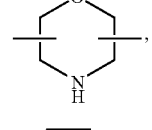

(Y10)

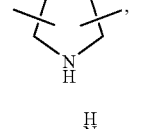

(Y11)

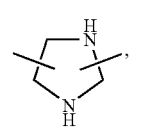

(Y12)

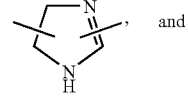 and (Y13)

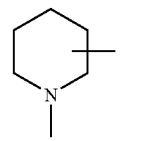

in formula (III), t, R$_4$ and X are as above defined.

2. The process according to claim 1, wherein the molar ratio of compounds of formulas (I):(II) is from 1 to 0.5 and the molar ratio of the compound of formula (II) dimethylaminopyridine (DMAP) is 1:1.

3. The process according to claim 1, wherein in the compounds of formula (I), $R_A$ is (Ia), (Ib) or (Ic), and the process is carried out in the presence of an additional equimolar amount of an inorganic or organic base selected from the group consisting of triethanolamine (TEA), pyridine, and N,N-diisopropylethylamine (DIPEA).

4. The process according to claim 1, wherein in formulae (II) and (III), Y is a straight or branched $C_1$-$C_{20}$ alkylene.

5. The process according to claim 1, which is carried out in presence of dimethylaminopyridine and a Lewis acid selected from the group consisting of bismuth triflate and scandium triflate.

6. The process according to claim 5, wherein the molar ratio of the compound of formula (II):dimethylaminopyridine (DMAP):scandium triflate ($Sc(OTf)_3$) is 1:1:0.1.

7. The process according to claim 5, wherein the Lewis acid is scandium triflate ($Sc(OTf)_3$).

8. The process according to claim 5, wherein in formulae (II) and (III), Y is b)

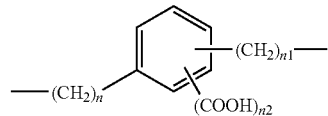

(2i)

wherein
n is an integer from 0 to 20,
n1 is 1,
n2 is 0;
with the proviso that the —$ONO_2$ group is linked to the —$(CH_2)_{n1}$— group.

9. The process according to claim 5, wherein in the compounds of formula (I), $R_A$ is (Ia), (Ib) or (Ic), and the process is carried out in the presence of an additional equimolar molar amount of an inorganic or organic base selected from the group consisting of triethanolamine (TEA), pyridine, and N,N-diisopropylethylamine (DIPEA).

* * * * *